US009220434B2

United States Patent
Snell et al.

(10) Patent No.: US 9,220,434 B2
(45) Date of Patent: Dec. 29, 2015

(54) SYSTEMS AND METHODS FOR SELECTIVELY UPDATING CARDIAC MORPHOLOGY DISCRIMINATION TEMPLATES FOR USE WITH IMPLANTABLE MEDICAL DEVICES

(75) Inventors: Jeffery D. Snell, Chatsworth, CA (US); Laurence S. Sloman, West Hollywood, CA (US); Bruce A. Morley, Acton, CA (US)

(73) Assignee: PACESETTER, INC., Sylmar, CA (US)

( * ) Notice: Subject to any disclaimer, the term of this patent is extended or adjusted under 35 U.S.C. 154(b) by 539 days.

(21) Appl. No.: 13/587,807

(22) Filed: Aug. 16, 2012

(65) Prior Publication Data

US 2014/0052012 A1  Feb. 20, 2014

(51) Int. Cl.
*A61N 1/39* (2006.01)
*A61B 5/0464* (2006.01)

(52) U.S. Cl.
CPC ............ *A61B 5/0464* (2013.01); *A61N 1/3925* (2013.01)

(58) Field of Classification Search
CPC ............................ A61B 5/0464; A61N 1/3925
See application file for complete search history.

(56) References Cited

U.S. PATENT DOCUMENTS

| 5,240,009 | A | 8/1993 | Williams |
|---|---|---|---|
| 5,273,049 | A | 12/1993 | Steinhaus et al. |
| 5,779,645 | A | 7/1998 | Olson et al. |
| 6,312,388 | B1 | 11/2001 | Marcovecchio et al. |
| 6,512,952 | B2 | 1/2003 | Stahmann et al. |
| 6,516,219 | B1 | 2/2003 | Street |
| 6,516,225 | B1 | 2/2003 | Florio |
| 6,628,986 | B1 | 9/2003 | Mouchawar et al. |
| 6,628,988 | B2 | 9/2003 | Kramer et al. |
| 6,636,764 | B1 | 10/2003 | Fain et al. |
| 6,643,546 | B2 | 11/2003 | Mathis et al. |
| 6,711,438 | B1 | 3/2004 | McClure et al. |
| 6,772,007 | B1 | 8/2004 | Kroll |
| 6,907,286 | B1 | 6/2005 | Kroll et al. |
| 6,996,434 | B2 | 2/2006 | Marcovecchio et al. |
| 7,058,450 | B2 | 6/2006 | Struble et al. |
| 7,146,213 | B1 | 12/2006 | Levine |
| 7,158,829 | B1 | 1/2007 | Levine |

(Continued)

FOREIGN PATENT DOCUMENTS

| EP | 1161179 B1 | 9/2004 |
|---|---|---|
| EP | 1339455 B1 | 2/2005 |

(Continued)

*Primary Examiner* — Amanda Patton

(57) ABSTRACT

Techniques are provided for updating a morphology template used to discriminate abnormal cardiac rhythms. In one example, a non-weighted candidate morphology template is generated based on far-field R-wave morphology. A weighted candidate morphology template is generated based on an ensemble average of the non-weighted candidate morphology template and a previous (i.e. active) morphology template. The previous morphology template is then selectively updated based on a comparison of additional R-waves against both the non-weighted and the weighted candidate templates. Thereafter, abnormal cardiac rhythms such as ventricular tachycardia and supraventricular tachycardia are discriminated using the updated morphology template based on newly-detected far-field R-waves. These techniques provide a method for updating the morphology discrimination template in response to long-term changes in morphology due to cardiac remodeling or cardiac disease progression.

16 Claims, 10 Drawing Sheets

(56) References Cited

U.S. PATENT DOCUMENTS

| | | |
|---|---|---|
| 7,171,268 B1 | 1/2007 | Kroll et al. |
| 7,174,210 B1 | 2/2007 | Levine |
| 7,184,834 B1 | 2/2007 | Levine |
| 7,191,002 B1 | 3/2007 | Kroll et al. |
| 7,245,967 B1 | 7/2007 | Shelchuk |
| 7,274,961 B1 | 9/2007 | Kroll et al. |
| 7,295,873 B1 | 11/2007 | Min et al. |
| 7,398,122 B1 | 7/2008 | Hofstadter et al. |
| 7,398,123 B1 | 7/2008 | Levine |
| 7,447,540 B1 | 11/2008 | Nabutovsky et al. |
| 7,450,995 B2 | 11/2008 | Moulder et al. |
| 7,653,436 B2 | 1/2010 | Schecter |
| 7,856,266 B1 | 12/2010 | Bornzin et al. |
| 7,974,687 B1 | 7/2011 | Farazi et al. |
| 7,991,459 B2 | 8/2011 | Palreddy et al. |
| 8,019,408 B2 | 9/2011 | Marcovecchio et al. |
| 8,165,675 B2 | 4/2012 | Wang et al. |
| 2002/0049474 A1 | 4/2002 | Marcovecchio et al. |
| 2002/0193695 A1 | 12/2002 | Koyrakh et al. |
| 2006/0079796 A1 | 4/2006 | Marcovecchio et al. |
| 2008/0306567 A1 | 12/2008 | Park et al. |
| 2009/0287268 A1 | 11/2009 | Nabutovsky et al. |

FOREIGN PATENT DOCUMENTS

| | | |
|---|---|---|
| WO | 0053088 | 9/2000 |
| WO | 0053089 | 9/2000 |

SYSTEMS AND METHODS FOR SELECTIVELY UPDATING CARDIAC MORPHOLOGY DISCRIMINATION TEMPLATES FOR USE WITH IMPLANTABLE MEDICAL DEVICES

FIELD OF THE INVENTION

The invention generally relates to implantable cardiac stimulation devices such as implantable cardioverter-defibrillators (ICDs) and, in particular, to techniques for updating morphology templates used by such devices to discriminate ventricular and supraventricular tachyarrhythmias.

BACKGROUND OF THE INVENTION

An ICD is a medical device for implant within a patient that recognizes various arrhythmias such as ventricular tachycardia (VT) and ventricular fibrillation (VF) and selectively delivers electrical shocks to terminate the arrhythmia. Prior to delivering therapy, it is important to distinguish a tachycardia arising in the ventricles from one arising elsewhere in the heart. A tachycardia arising in the ventricles (referred to as VT) is often more serious than a tachycardia arising elsewhere in the heart since VT can sometimes lead to VF, which can be fatal if untreated. In contrast, a supraventricular (SVT) is a tachyarrhythmia whose origin is above the ventricles but which is conducted to the ventricles resulting in unacceptably rapid ventricular rate. The true underlying arrhythmia of SVT may be, e.g., atrial fibrillation (AF), sinus tachycardia (ST), ectopic atrial tachycardia, atrial reentry tachycardia, atrioventricular (AV) nodal reentry tachycardia, paroxysmal AF or atrial flutter. Failure to distinguish SVT from VT can result in delivery of inappropriate therapy. Depending upon the capabilities of the ICD, inappropriate therapy might involve delivery of unnecessary and painful electrical shocks to the heart or improper delivery of anti-tachycardia pacing (ATP.) Misidentification of SVT and VT is one of the leading causes of improper device therapy.

Accordingly, it is desirable to efficiently and reliably distinguish SVT from VT. Some discrimination techniques used by state-of-the-art ICDs analyze the morphology of a ventricular intracardiac electrogram (IEGM) to distinguish SVT from VT. The ventricular IEGM is an electrical signal sensed internally by the device, which is associated with the contraction and expansion of the ventricular chambers of the heart. More specifically, the contraction of ventricular muscle tissue is triggered by the depolarization of the ventricles, which is manifest within the ventricular IEGM as an R-wave (also referred to as the "QRS complex.") Repolarization of the ventricles is manifest as a T-wave in the ventricular IEGM. Note that the contraction of atrial muscle tissue also generates electrical signals. Specifically, the contraction of the atria is triggered by the electrical depolarization of the atria, which is manifest as a P-wave in the IEGM. A similar repolarization of the atrial tissue usually does not result in a detectable signal within the IEGM because it coincides with, and is obscured by, the R-wave. For the purposes of discriminating SVT from VT, the atrial signals are typically ignored and only ventricular signals are examined. (Note that the terms P-wave, R-wave and T-wave may also be used to refer to corresponding features of a surface electrocardiogram (ECG.) Herein, however, these terms are primarily used to refer to features of the IEGM.)

Morphological discrimination of VT and SVT typically exploits the fact that R-waves occurring during a tachycardia of ventricular origin have a different shape from R-waves triggered from normal atrio-ventricular conduction from the atria. This is because the sequence of activation of the ventricular cardiac muscles differs depending on whether the trigger source is within the ventricles (as opposed to via the normal AV conduction mechanism.) Accordingly, morphologic discrimination procedures typically record R-wave morphology during normal sinus rhythm and then generate and save a morphology template based on the sinus rhythm R-wave for use during tachycardia. If a tachycardia is detected (based on the ventricular rate exceeding a VT threshold), the R-waves during the tachycardia are compared against the template. If there is a substantial match, the tachycardia is deemed SVT and no ventricular shock or ATP therapy is delivered. Instead, other forms of therapy might be delivered to address the SVT. On the other hand, if there is no match the tachycardia is deemed to be VT or VF and so ATP therapy or a shock might be delivered. In some devices, if the rate exceeds a higher VF threshold, a defibrillation shock is promptly delivered regardless of waveform morphology under the assumption that the arrhythmia is a potentially fatal VF. See, for example, techniques described in U.S. Pat. No. 7,974,687 to Farazi et al., entitled "Methods and Systems for Enhanced Arrhythmia Discrimination."

Various waveform discrimination techniques are described in, e.g., U.S. Pat. No. 5,273,049 to Steinhaus et al. entitled, "Detection of Cardiac Arrhythmias using Template Matching by Signature Analysis"; U.S. Pat. No. 5,240,009 to Williams, entitled "Medical Device with Morphology Discrimination"; U.S. Pat. No. 5,779,645 to Olson et al., "System and Method for Waveform Morphology Comparison," and U.S. Pat. No. 6,516,219 to Street, entitled "Arrhythmia Forecasting based on Morphology Changes in Intracardiac Electrograms." See, also, the morphological discrimination techniques described in U.S. patent application Ser. No. 11/674,974, filed Feb. 14, 2007 of Graumann, entitled "System and Method for Morphology-Based Arrhythmia Discrimination using Left Ventricular Signals sensed by an Implantable Medical Device."

Note that during normal sinus rhythm—in particular when the aforementioned template is being generated—a certain amount of variability in R-wave morphology is normal. The variability is caused by a variety of factors, including changes in posture, diurnal variations and other physiological variables. Thus, throughout the day the R-wave will have a central or average morphology but specific R-waves will have varying morphology around this average. Over a longer period there can be other fundamental changes to the central or average R-wave morphology due to effects such as cardiac remodeling, cardiac disease progression, ischemia, etc. For this reason, the morphology template should be periodically updated to reflect the current sinus R-wave morphology. Accordingly, a template update process can be used to periodically record and save the shape of R-waves for use as a template. The time of each template update is based on a clock timer. When the timer expires, a template update process is initiated to generate and record a new template. When the template update process records the new template, a number of rules may be applied to ensure that the complex saved is, in fact, an R-wave rather than a premature ventricular contraction (PVC), noise artifact or some other signal.

Even when such rules are applied, complications can arise due to the variability of R-wave morphology. In particular, at the time of a template update, the R-wave morphology may be near its central value or it may be at an extreme of its variation for the patient or somewhere in-between. Similarly, when a tachycardia occurs, the R-wave morphology may be at or near its central value or it may be at an extreme of its variation for the patient or somewhere in-between. For example, if the template waveform is acquired at one extreme of the R-wave morphology variation and a subsequent SVT occurs at the opposite extreme of the R-wave morphology variation, then the comparison of the template to the tachycardia R-wave will reflect the full extent of the different waveform morphologies. This might result in possible misidentification of the SVT as a VT because the R-waves during SVT might not match the template R-wave, although both are supraventricular in origin. In this regard, the closer the template is to a central value for the R-wave morphology (as opposed to an extreme), the more likely that a correct SVT determination will be made.

Accordingly, it would be desirable to provide improved techniques for updating morphology templates that avoid these and other problems.

SUMMARY OF THE INVENTION

In an exemplary embodiment, a method is provided for use with an implantable cardiac stimulation device such as an ICD for updating a morphology template used to discriminate among cardiac rhythms within a patient. In one example, cardiac signals are detected within the patient, cardiac rhythm morphology is assessed and a first (non-weighted) candidate morphology template is generated based on the cardiac rhythm morphology. A second (weighted) candidate morphology template is generated based on an ensemble average of the first (non-weighted) candidate morphology template and a previous (i.e. active) morphology template. The previous morphology template is then selectively updated based on a comparison of additional cardiac rhythm morphology with both the first (non-weighted) and second (weighted) candidate morphology templates. Thereafter, abnormal cardiac rhythms are discriminated within the patient using the selectively-updated morphology template.

In an illustrative embodiment, the non-weighted candidate template is generated by: identifying ventricular depolarization waveforms within the cardiac signals for a plurality of sinus rhythm ventricular depolarization events (i.e. sinus R-waves); identifying fiducial points within the depolarization waveforms; aligning the waveforms from the plurality of depolarization events using corresponding fiducial points; and then ensemble averaging the aligned waveforms to yield the non-weighted candidate waveform. The weighted candidate template is generated by: identifying corresponding fiducial points within the non-weighted candidate template and the active template; aligning the non-weighted candidate template with the active template using the corresponding fiducial points; and then ensemble averaging the aligned templates to yield a weighted candidate template.

In the illustrative embodiment, the active (i.e. old) template is selectively updated by: (a) replacing the active template with the weighted candidate template if the newly-detected ventricular depolarization events substantially match the weighted candidate template and (b) replacing the active template with the non-weighted candidate template if the newly-detected ventricular events substantially match the non-weighted candidate template but not the weighted candidate template. If the newly-detected ventricular depolarization events do not substantially match either the non-weighted or the weighted candidate templates, the active template is retained and a warning indicator is generated. In this manner, rather than just replacing the active template with a single new template, two candidate templates are created: a weighted template based on an ensemble average of the current R-wave morphology with the active template; and a non-weighted template based on only the current R-wave morphology. The candidate templates are validated by comparison with the morphology of newly-detected sinus rhythm R-waves. The aforementioned validation may be summarized as follows:

Case 1: If the weighted candidate template matches the current (sinus) R-waves, then the weighted template is installed as the new template.

Case 2: If the weighted candidate template does not match the current (sinus) R-waves but the non-weighted candidate template instead matches, the non-weighted template is installed as the new template.

Case 3: If neither candidate template matches the current (sinus) R-waves then no change is made to the template pending further processing.

Case 1 is the typical case where minimal changes have occurred to R-wave morphology since the previous template update and so the weighted template is used, which is weighted toward the shape of the active template. As more and more such updates occur, the active template thereby gravitates to the central average R-wave shape. Because the active template obtains this central shape then—even if a tachycardia occurs when the R-wave is at the extreme of its variability—the difference between the active template and the sinus R-wave is minimized and the comparison is robust. Case 2 describes the less typical situation where a physiological effect has changed the fundamental morphology of the sinus R-wave. In this case, the weighted candidate template (which is weighted toward the shape of the previous template) will no longer resemble current sinus morphology. In this situation, the non-weighted template is installed as the new template, thereby reflecting the recent fundamental change in morphology. If noise or other artifacts have affected the system such that neither candidate template matches the current sinus morphology, then the template update is discarded (Case 3) pending further processing or analysis.

Hence, the illustrative embodiments provide a method for reliably obtaining a central value for R-wave morphology for the purposes of updating a morphology discrimination template, which also serves to update the template appropriately when there are longer-term changes in morphology due to effects such as cardiac remodeling, cardiac disease progression, etc. This helps provide accurate and reliable discrimination of SVT from VT so that therapy can be delivered appropriately. During routine use, the ventricular rate is tracked to detect a tachycardia based on a VT rate threshold. If tachycardia is indicated, the device uses the current (active) template to discriminate the tachycardia (i.e. to distinguish VT from SVT) so that appropriate therapy can be delivered. In some implementations, if the ventricular rate exceeds a higher VF rate, a defibrillation shock is immediately delivered as VF is life-threatening.

System and method implementations of these and other techniques are presented herein by way of examples wherein the implantable device is equipped for performing pacing, defibrillation and cardiac resynchronization therapy (CRT) functions.

BRIEF DESCRIPTION OF THE DRAWINGS

Features and advantages of the described implementations can be more readily understood by reference to the following description taken in conjunction with the accompanying drawings.

DETAILED DESCRIPTION OF THE PREFERRED EMBODIMENTS

The following description includes the best mode presently contemplated for practicing the invention. This description is not to be taken in a limiting sense but is made merely to describe general principles of the invention. The scope of the invention should be ascertained with reference to the issued claims. In the description of the invention that follows, like numerals or reference designators will be used to refer to like parts or elements throughout.

Overview of Implantable System

Figure 1:
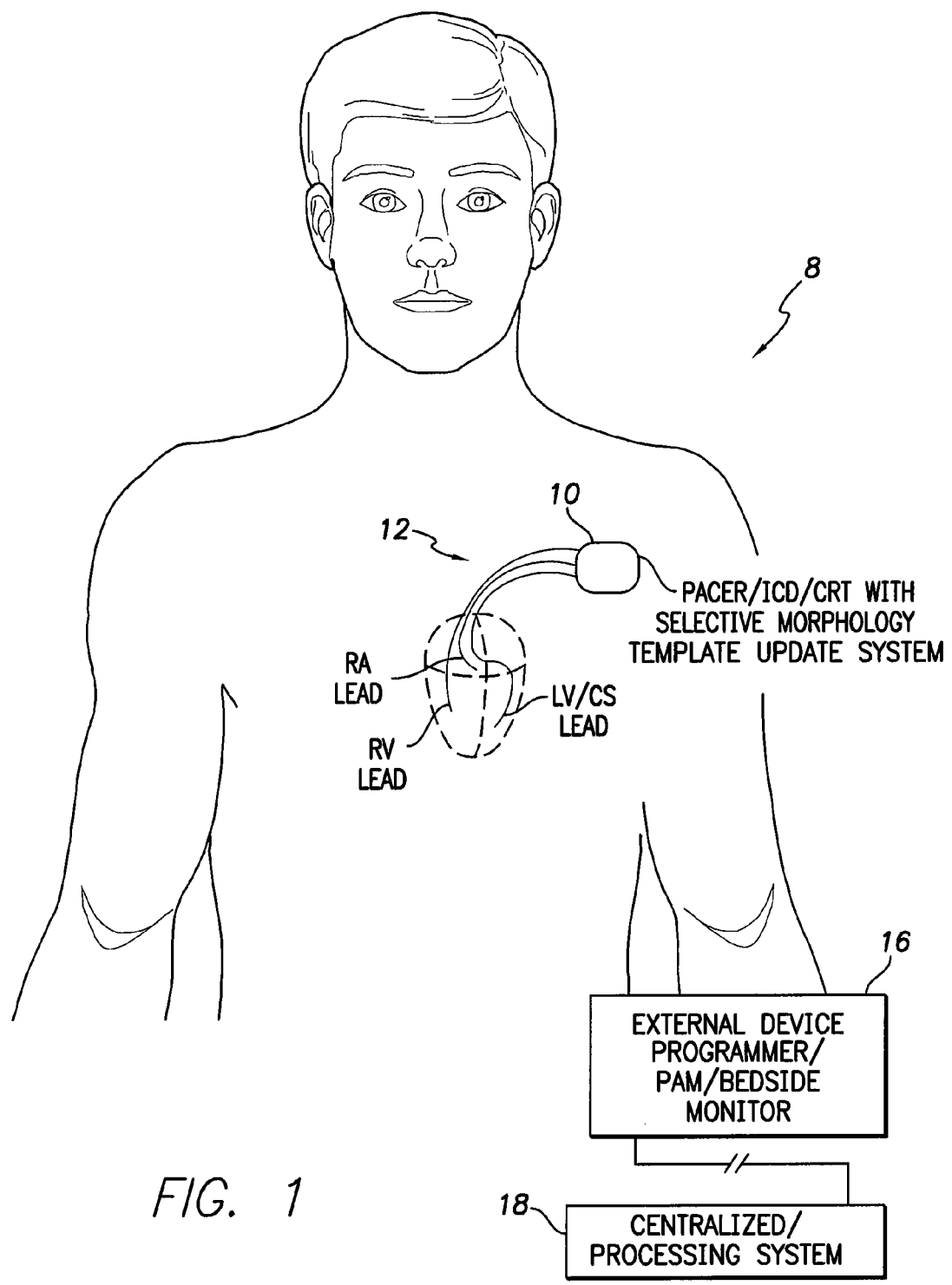
FIG. 1 illustrates components of an implantable medical system having an ICD or other device equipped with a selective morphology template update system.

FIG. 1 illustrates an implantable medical system 8 capable of selectively updating an R-wave morphology template for use in SVT/VT discrimination wherein the template is updated so as to represent a central value for R-wave morphology while taking into account longer-term changes in morphology due to effects such as cardiac remodeling, cardiac disease progression. In this particular example, the implantable medical system 8 includes a pacer/ICD/CRT 10 or other implantable cardiac rhythm management device equipped with a set of cardiac sensing/pacing leads 12 implanted on or within the heart of the patient, including an LV lead implanted via the CS. In FIG. 1, a stylized representation of the set of leads is provided. More accurate illustrations of the leads are provided within FIG. 9. Although identified as a "pacer/ICD/CRT" in FIG. 1, it should be understood that device 10 can be any suitably-equipped implantable medical device, such as a standalone pacemaker, ICD or CRT device, including CRT-D and CRT-P devices. In the following, for brevity, device 10 will be referred to simply as a pacer/ICD.

Preferably, the pacer/ICD itself performs the template update procedure. In some implementations, however, the device might additionally or alternatively transmit pertinent electrocardiac parameters to an external device 16, which performs or supervises the template update. Template updates performed by the pacer/ICD itself are preferred as that allows for frequent updating of the template. However, updating using an external system might be appropriate in some instances, such as during a post-implant follow-up session with a clinician. Note also that other external systems might instead be used such as bedside monitors or the like. In some embodiments, the external system is directly networked with a centralized computing system, such as the HouseCall™ system or the Merlin@home—Merlin.Net systems of St. Jude Medical.

Exemplary Template Update Techniques

Figure 2:
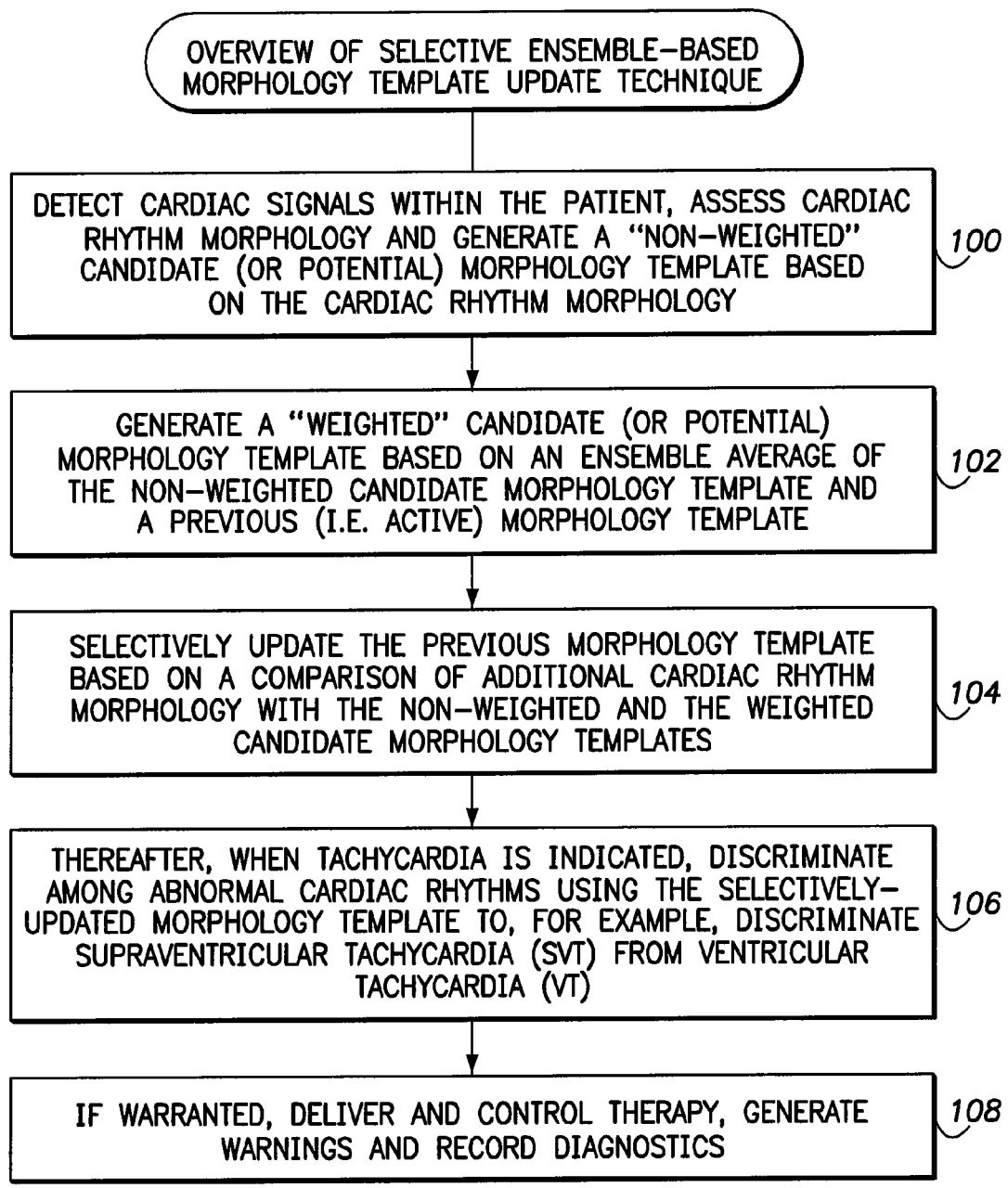
FIG. 2 summarizes a selective morphology template update technique that may be performed by the system of FIG. 1.

FIG. 2 broadly summarizes techniques exploited by the pacer/ICD of FIG. 1 (or other suitably-equipped systems) for updating an R-wave template for SVT/VT discrimination or other purposes. Beginning at step 100, the pacer/ICD detects electrical cardiac signals within the patient, assesses cardiac rhythm morphology and generates a non-weighted candidate (or potential) morphology template based on the cardiac rhythm morphology (i.e. the device generates the first candidate template.) Typically, this is performed using ventricular IEGM signals to generate a candidate morphology template representative of R-waves, but principles of the technique may be broadly applicable to generating templates for discriminating other cardiac signal waveforms such as P-waves or T-waves. At step 102, the device generates a weighted candidate (or potential) morphology template based on an ensemble average of the non-weighted candidate morphology template and a previous (i.e. active) morphology template (i.e. the device generates the second candidate template.) At step 104, the device selectively updates the previous (active) morphology template based on a comparison of additional cardiac rhythm morphology signals with both the non-weighted and the weighted candidate morphology templates. As will be explained, the selective update is preferably performed so as to generate a new template representative of a central value of the morphology to be analyzed (e.g. R-wave morphology.)

Thereafter, at step 106, when tachycardia is indicated the device then discriminates among abnormal cardiac rhythms within the patient using the selectively-updated morphology template to, for example, discriminate SVT from VT. For example, the current ventricular rate may be tracked and compared against a VT threshold of 120 bpm and, if the threshold is exceeded, a tachycardia is thereby indicated. At step 108, the device then, if warranted, delivers and controls therapy, generates warning signals and records diagnostics. The therapy to be delivered may include, for example, ATP, atrial cardioversion or ventricular defibrillation. ATP is discussed in, e.g., in U.S. Pat. Nos. 6,907,286, 7,191,002 and 7,295,873. Cardioversion and defibrillation therapies are discussed in, e.g., U.S. Pat. Nos. 6,772,007, 7,856,266, 7,450, 995, 7,398,122, 7,171,268, and 6,628,986. See, also, therapeutic techniques described in U.S. Pat. No. 7,245,967. Note also that, if the ventricular rate exceeds a high threshold indicative of VF, one or more defibrillation shocks will typically be delivered without any discrimination of VT from SVT, since VF is life-threatening. Turning now to FIGS. 3-8, more detailed examples of the general method of FIG. 2 will be described.

Figures 1, 3:
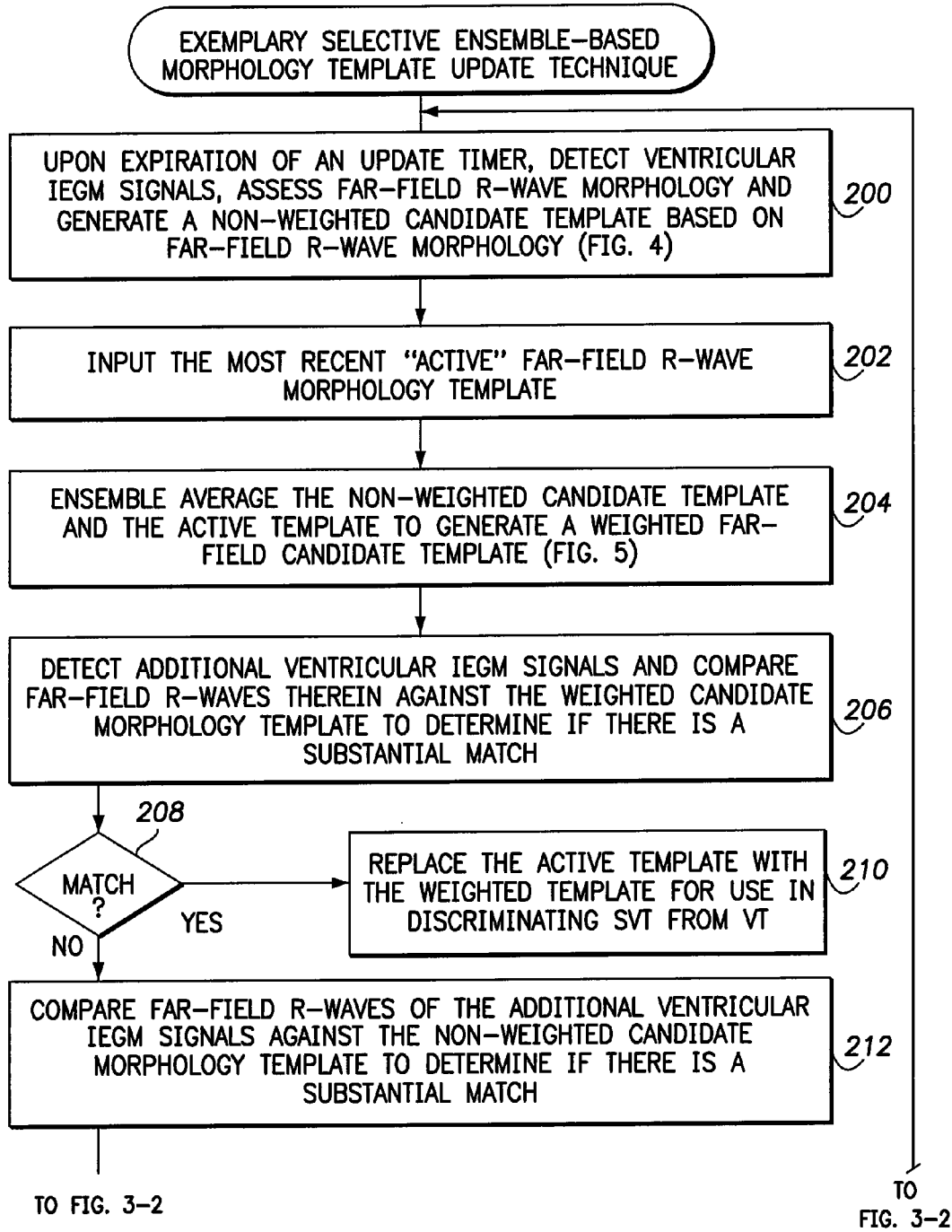
FIG. 3 illustrates an exemplary template update procedure for use with the method of FIG. 2, wherein an active template is selectively updated based on a comparison of weighted and non-weighted candidate templates.
Figures 2, 3:
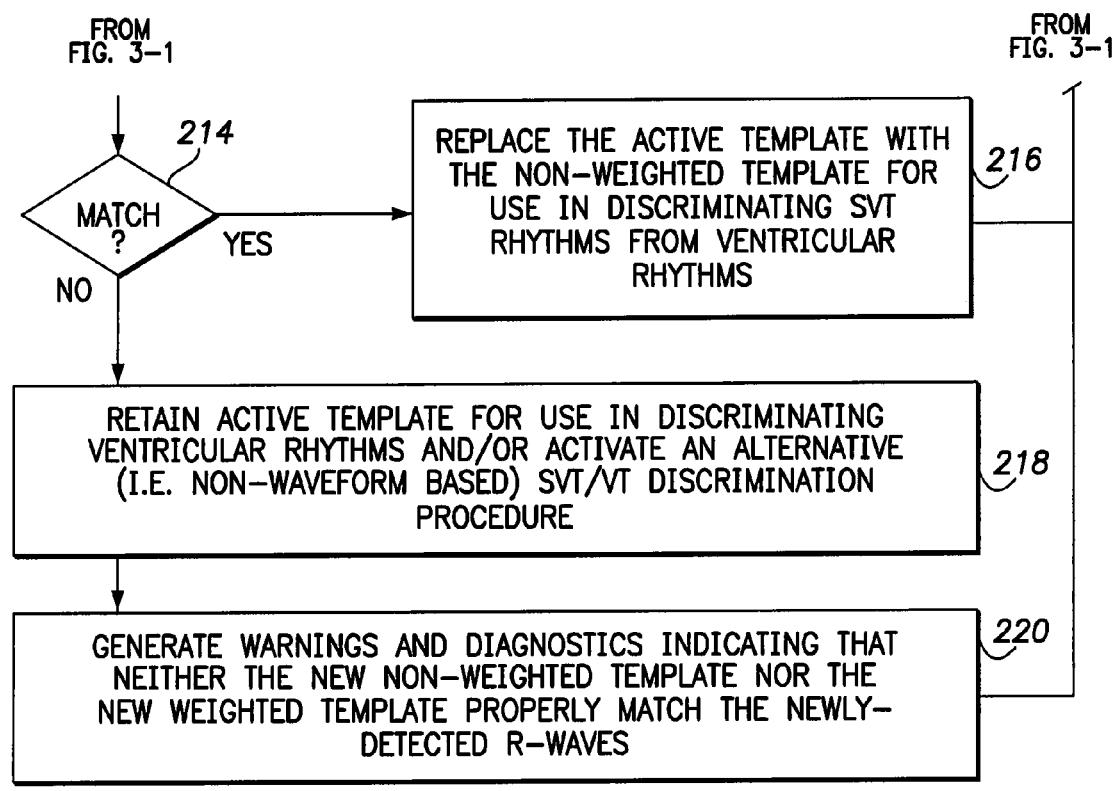

FIG. 3 illustrates an example for use in updating R-wave templates for SVT/VT discrimination wherein an active template is selectively updated based on a comparison of newly-detected far-field R-wave morphology with weighted and non-weighted templates. At step 200, upon expiration of an update timer, the pacer/ICD detects ventricular IEGM signals, assesses far-field R-wave morphology (from a plurality of far-field R-waves) and generates a non-weighted candidate template based on far-field R-wave morphology (i.e. the device generates the first candidate template.) The update timer may be set, for example, to update the templates six to ten times per day. The far-field ventricular IEGM signals may be detected by using a bipolar LV or RV lead in a unipolar mode to sense signals between the tip electrode of the lead and the device "can" or housing electrode. Details of the actual technique for generating the non-weighted template based on far-field signals are discussed below with reference to FIG. 4. At step 202, the device inputs the most recent "active" far-field R-wave morphology template, i.e. the template currently being used by the device to discriminate SVT from VT. If this is the first iteration of this update procedure, the initial far-field R-wave template may be a default template pre-programmed within the device. At step 204, the device ensemble averages the non-weighted candidate template generated at step 200 and the active template input at step 202 to generate or produce a weighted far-field candidate template (i.e. the second candidate template) using techniques to be described with reference to FIG. 5. Alternatively, if there is no active template, then the weighted candidate template is not created and only the non-weighted candidate template is generated and considered for use as the new active template.

Continuing with the example where both weighted and non-weighted candidate templates are generated, the pacer/ICD then proceeds to update the active template based on a comparison of newly-detected far-field R-waves with the candidate templates. Hence, at step 206, the device detects additional ventricular IEGM signals and compares far-field R-waves detected therein against the weighted candidate morphology template to determine if there is a substantial match, i.e. to determine whether the weighted candidate template adequately represents the shape of the newly-detected R-waves. The determination of a "substantial match" may be made based on otherwise conventional waveform matching techniques, such as by assessing a metric representative of a cumulative difference between the newly-detected R-waves and the weighted candidate template and then comparing that metric against a threshold indicative of a substantial match. The threshold can be pre-programmed within the device or generated using other suitable techniques and may be expressed, e.g., as a percentage difference. If the metric is below the threshold (i.e. any differences between newly-detected R-waves and the weighted candidate template are relatively small), the device concludes there is a substantial match. Conversely, if the metric exceeds the threshold (i.e. the differences between the newly-detected R-waves and the weighted candidate template are significant), the device concludes there is no substantial match. (As can be appreciated, in other examples, the metric and the threshold could instead be defined so that the metric would need to exceed the threshold to indicate a substantial match, rather than vice versa. That is, various threshold comparison procedures could be used that are logically or mathematically equivalent.) See, also, template matching techniques described in U.S. Pat. No. 6,516,225 of Florio.

If a match is found at step 208, the device then replaces the active template with the weighted template, at step 210, for use in discriminating SVT from VT. This is the typical case wherein there is relative minimal change in R-wave morphology from the prior update and so the active template is replaced with a modified version of the active template, adjusted to account for modest changes in R-wave morphology. If the weighted template does not adequately match the newly-detected far-field R-waves, then at step 212, the pacer/ICD compares the newly-detect far-field R-waves detected at step 206 against the non-weighted candidate morphology template generated at step 204 to determine if there is a substantial match. Again, this determination may be made by generating a suitable metric for comparison against an appropriate threshold. If a match is found, at step 214, the device then replaces the active template with the non-weighted template, at step 216, for use in discriminating SVT from VT. This is the case where there has been a profound or significant change in R-wave morphology from the last template update and the active template is therefore replaced with the new non-weighted template. In the event that neither the weighted template nor the non-weighted template adequately matches the newly-detected R-waves, the device retains the active template at step 218 and generates suitable warning signals and diagnostic information at step 220. The warnings and diagnostics inform the clinician that neither the new non-weighted template nor the new weighted template properly matched the newly-detected R-waves. The clinician can then adjust the "match" thresholds, if needed, or take other actions to address the problem.

Additionally or alternatively, a different SVT/VT discrimination technique may be activated at step 218 (assuming the device is so equipped) to provide for continued SVT/VT discrimination in cases where neither of the candidate templates match the newly-detected R-waves. Other techniques for distinguishing VT and SVT that do not necessarily require morphological waveform discrimination include "sudden onset discrimination" and "PR logic discrimination." Sudden onset discrimination is discussed, e.g., in U.S. Pat. No. 6,636,764 to Fain et al., entitled "Safety Backup in Arrhythmia Discrimination Algorithm." PR logic discrimination is discussed, e.g., in U.S. Pat. No. 7,058,450 to Struble et al., entitled "Organizing Data according to Cardiac Rhythm Type." See, also, U.S. Pat. No. 8,165,675 of Wang et al., entitled "Systems and Methods for use with an Implantable Medical Device for Discriminating VT and SVT based on Ventricular Depolarization Event Timing" and techniques described in U.S. Published Application 2011/0282405 of Hauck et al., entitled "Systems and Methods for use with an Implantable Medical Device for Discriminating VT and SVT by Selectively Adjusting Atrial Channel Sensing Parameters."

See, also, techniques discussed in: U.S. Pat. No. 7,447,540 of Nabutovsky et al., entitled "Systems and Methods for Detection of VT and VF from Remote Sensing Electrodes"; U.S. Patent Application 2009/0287268 also of Nabutovsky et al., entitled "Methods and Systems for Improved Arrhythmia Discrimination"; U.S. Pat. No. 7,274,961 to Kroll et al., entitled "Implantable Cardiac Stimulation Device and Method that Discriminates between and Treats Ventricular Tachycardia and Ventricular Fibrillation"; U.S. Pat. No. 7,398,123 to Levine, entitled "Methods and Devices for Reducing the Detection of Inappropriate Physiologic Signals to Reduce Misdiagnosis of Normal Rhythms as Tachyarrhythmias"; and U.S. Pat. No. 6,711,438 to McClure et al., entitled "Method and Apparatus for Blanking T-waves from Combipolar Atrial Cardiac Signals based on Expected T-wave Locations." See, also, U.S. Pat. Nos. 7,146,213; 7,158,829; 7,174,210; and 7,184,834 to Levine, entitled "Method and Apparatus for Improving Specificity of Tachycardia Detection Techniques in Dual-unipolar and Dual-Bipolar Implantable Cardiac Stimulation Systems."

Following steps 210, 216 or 220, the update timer is reset and the overall update procedure eventually repeats once the timer again expires. In the event that no match is detected (steps 218 and 220), the update procedure may be repeated immediately to attempt another update of the template.

Figure 4:
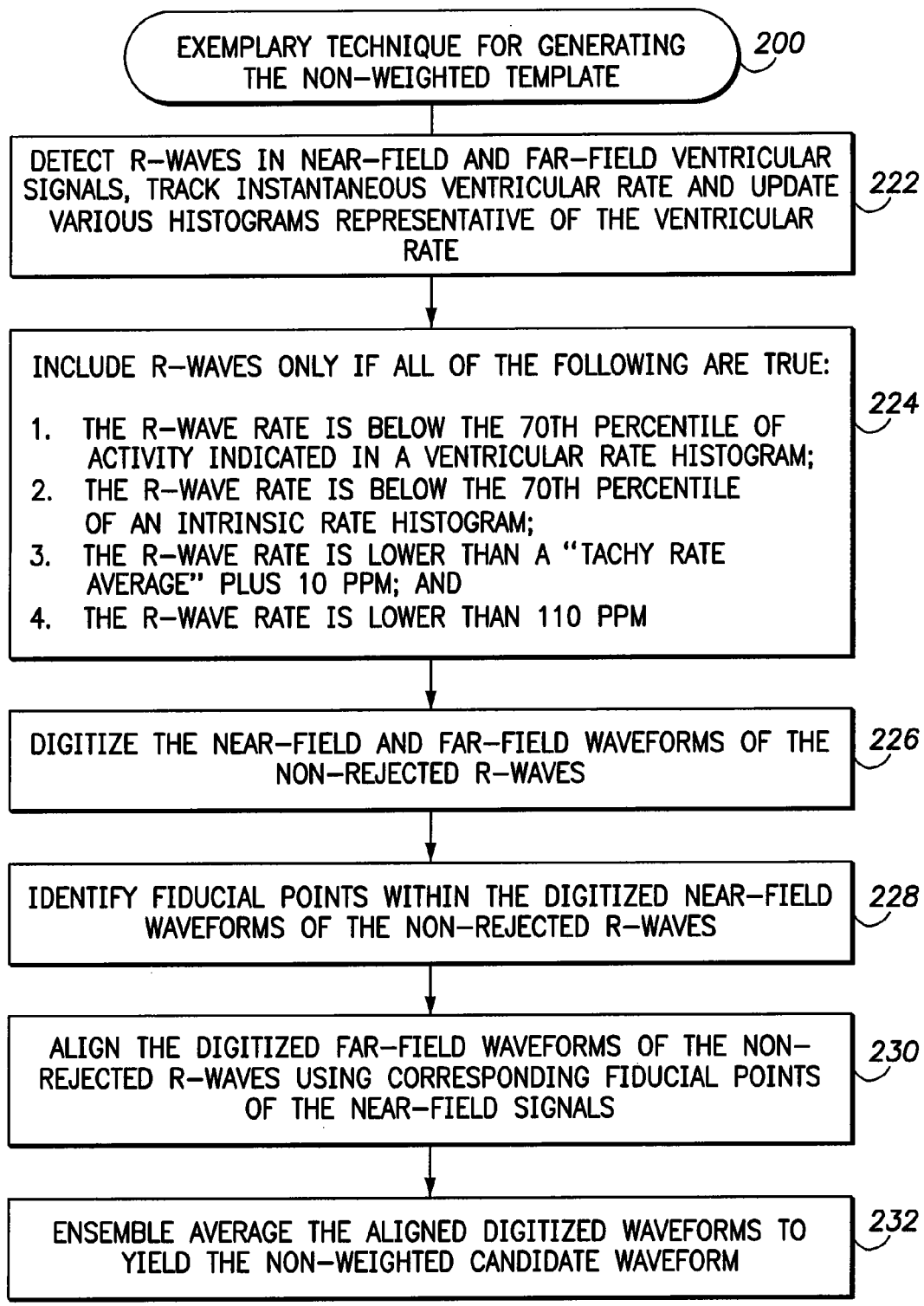
FIG. 4 illustrates an exemplary procedure for use with the method of FIG. 3 for generating the non-weighted template.

FIG. 4 illustrates techniques for use at step 200 of FIG. 3 for generating the non-weighted template. Note that during the template update process, individual far-field IEGM waveforms are collected and ensemble averaged to reduce noise and smooth out beat-to-beat variability due to short term effects such as respiration. During the individual waveform collection process, waveforms are rejected according to a set of rules to ensure that a majority of the waveforms are sinus R-waves. These rules are based on rate. To include the current waveform in the ensemble all of these rules must be true:

1. The R-wave rate (instantaneous rate) must be below the $70^{th}$ percentile of activity-indicated rate histogram;
2. The R-wave rate (instantaneous rate) must be below the $70^{th}$ percentile of (intrinsic) rate histogram;
3. The R-wave rate (instantaneous rate) must be lower than the "Tachy Rate Average"+10 pulses per minute (ppm);
4. The R-wave rate (instantaneous rate) must be lower than 110 ppm.

Accordingly, at step 222, the pacer/ICD detects R-waves within near-field and far-field ventricular IEGM signals, tracks the instantaneous ventricular rate based on the R-waves (i.e. the rate determined from the latest R-R interval), and creates or updates various histograms representative of the ventricular rate (such as an intrinsic rate histogram representative of the distribution of intrinsic ventricular beats, and an activity-indicated rate histogram representative of the ventricular rate during periods of patient activity.) As noted, far-field ventricular IEGMs can be derived from unipolar signals. Near-field ventricular IEGMs are instead generated by using the LV or RV lead in a bipolar mode, i.e. by sensing electrical signals tip to ring. At 224, the device analyzes each R-wave to determine whether it should be used in the procedure to generate the non-weighted template. In particular, the device rejects the R-wave if it is unsuitable for any of the reasons listed above. As shown in the figure, the device includes an R-wave only if each of the following is true: (1) the instantaneous R-wave rate is below the 70th percentile of activity-indicated in a ventricular rate histogram; (2) the instantaneous R-wave rate is below the 70th percentile of an intrinsic rate histogram; (3) the instantaneous R-wave rate is lower than a "tachycardia rate average" plus 10 ppm (or other suitable offset); and (4) the R-wave rate is lower than 110 ppm. (Note that, in some examples, the "tachycardia rate average" might be calculated as the average rate for R-waves having instantaneous rates above the aforementioned VT rate threshold. Other suitable definitions may instead be used.) The criteria of step 224 ensure that only R-waves likely to be associated with a sinus rhythm are used for generating the template.

At step 226, the pacer/ICD then digitizes the near-field and far-field waveforms of the non-rejected R-waves using otherwise conventional techniques and, at step 228, identifies certain predetermined fiducial points within the digitized waveforms of the near-field R-waves. (Alternatively, the device might instead digitize all waveforms and then discard those that correspond to rejected R-waves.) For example, suitable fiducial points may be the peak of the near-field R-wave, or its beginning and end points. At step 230, the device aligns the digitized far-field waveforms of the non-rejected R-waves using corresponding fiducial points obtained from the near-field signals. For example, the device may align the digitized far-field R-waves based on their near-field peaks. At step 232, the device then ensemble averages the aligned digitized far-field waveforms to yield the non-weighted far-field candidate waveform. Preferably, each point in the template ensemble average is an average of the same point in eight collected waveforms. An efficient technique for generating ensemble averages is discussed below with reference to FIG. 8.

Figure 5:
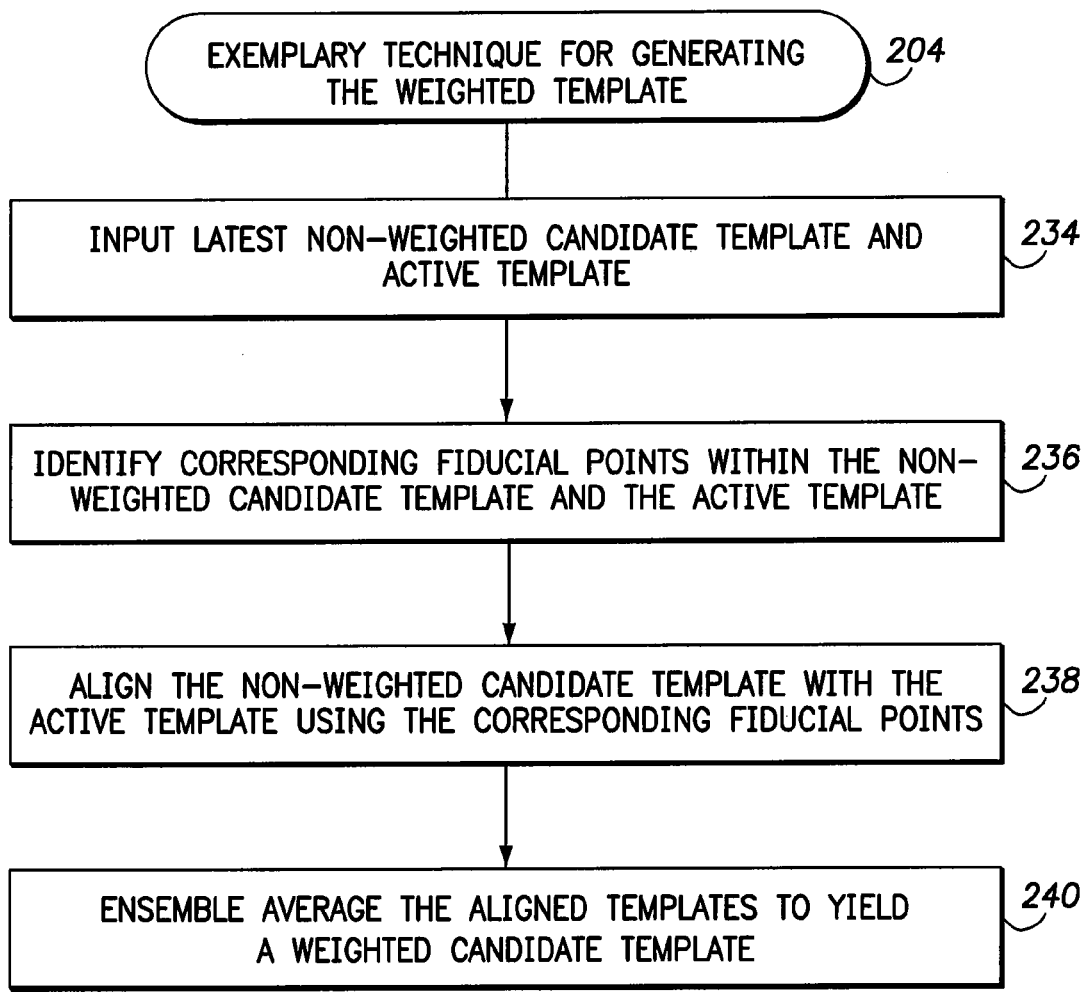
FIG. 5 illustrates an exemplary procedure for use with the method of FIG. 3 for generating the weighted template.

FIG. 5 illustrates techniques for use at step 204 of FIG. 3 for generating the weighted template. At step 234, the pacer/ICD inputs the latest non-weighted candidate template (generating at step 200 of FIG. 3) and the active template (input at step 202 of FIG. 3.) At step 236, the device identifies corresponding fiducial points within the non-weighted candidate template and the active template. At step 238, the device aligns the non-weighted candidate template with the active template using the corresponding fiducial points and, at step 240, ensemble averages the aligned templates to yield the weighted candidate template. Preferably, the weighted template is weighted heavily toward the active template. For example, the weighted template may be generated as 1/16th of the non-weighted template and 15/16th of the active template.

Figure 6:
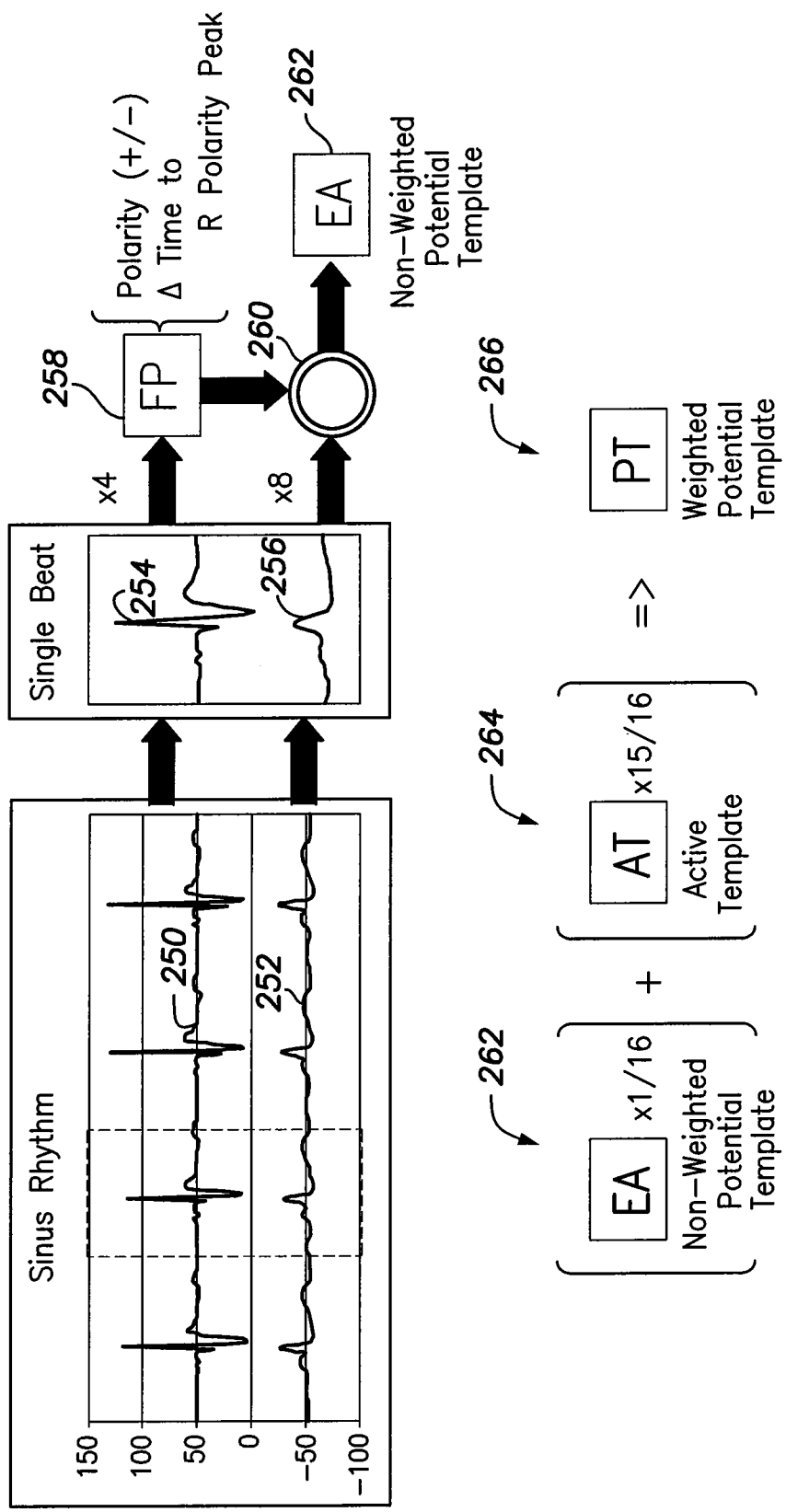
FIG. 6 is a schematic illustration of the exemplary procedures of FIGS. 4-5 for generating the weighted and non-weighted templates.

The techniques of FIGS. 3-5 are schematically illustrated by way of the diagrams of FIG. 6. Briefly, a graphic illustration of a bipolar (near-field) ventricular IEGM 250 is shown along with a corresponding unipolar (far-field) ventricular IEGM 252. As already explained, the near-field signals are used to identify fiducial points for use in aligning the waveforms but the template is actually generated based on the far-field version of the R-waves. Individual R-waves are identified within the far-field and near-field IEGMs (254 and 256, respectively.) Fiducial points (FPs) are detected or identified within the near-field R-wave as represented schematically by FP processing block 258. In this example, the fiducial point analysis takes into account polarity (i.e. the device verifies that the R-waves to be ensemble averaged have the same polarity) as well as a value referred to as "Δ time to R polarity peak," which is the time it takes to find the peak value of the R wave in the direction of the selected polarity (i.e. time to max R-waveform value for positive polarity or time to min R-waveform value for negative polarity). (Note that the R-wave may continue after the peak detection point depending on variables such as lead configuration, which affects the shape of the R-wave, desired peak polarity, etc.) The fiducial points are then used to align eight of the most recent far-field R-waves for ensemble averaging, as represented by averaging process 260. The resulting ensemble average is the non-weighted candidate (or "potential") template 262. The non-weighted candidate template 262 is then ensemble added to the active template 264 to yield the weighted candidate (or potential) template 266. In this particular example, the active template is weighted as 15/16's in the resulting template; whereas the non-weighted template is weighted only 1/16 in the resulting template. That is, the weighted template is heavily weighted in favor of the active template over the non-weighted template.

Figure 7:
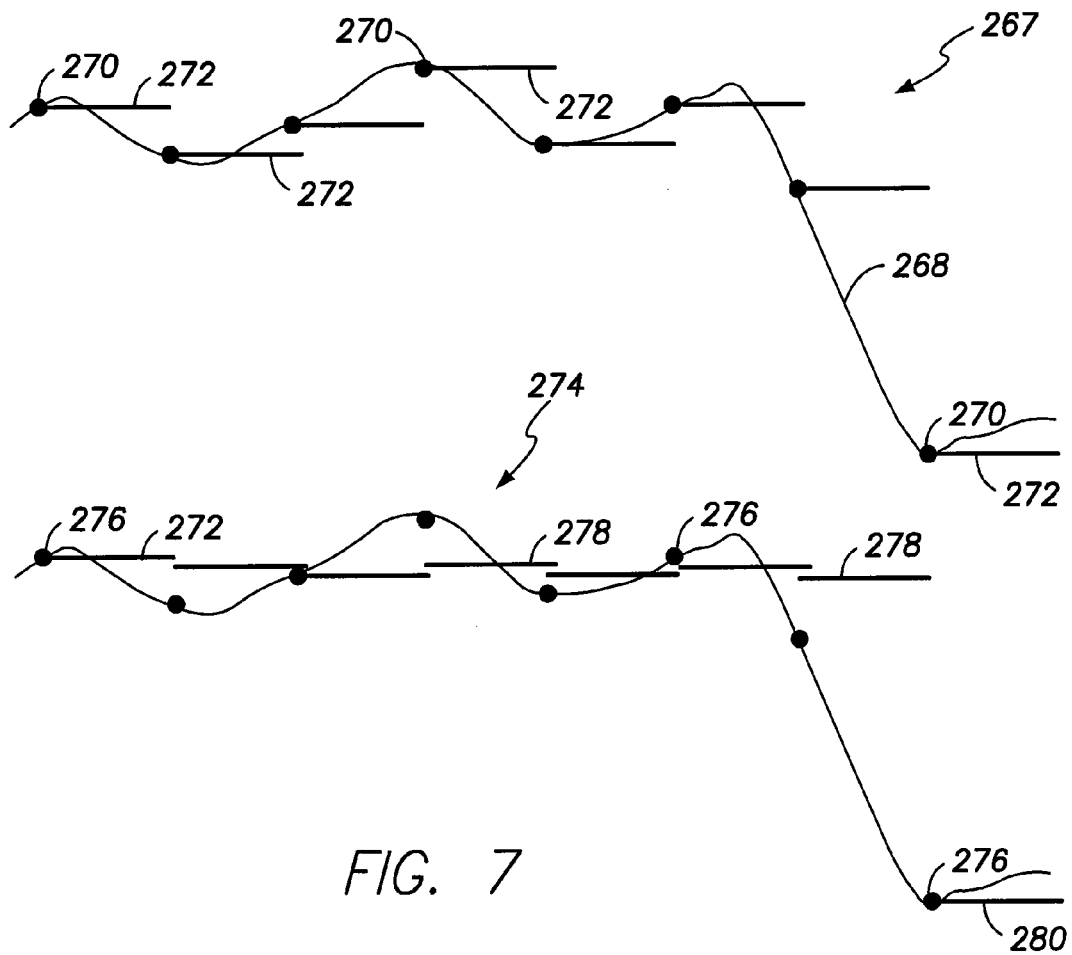
FIG. 7 graphically illustrates waveform morphology variability addressed by the techniques of FIGS. 3-6.

FIG. 7 graphically illustrates waveform morphology variability exploited by the techniques of FIGS. 3-5. Graph 267 illustrates the effect of simply replacing the active template with a new template at each template update (i.e. without performing the selective updating technique.) The curve 268 provides an abstract representation of the variation in R-wave morphology (y-axis) over time (x-axis.) The R-wave morphology varies throughout the day due to many factors including posture, activity and physiologic diurnal variations. The template update is performed at regular intervals. During some of the updates, the R-wave morphology may be at a local peak or valley, at other times it may be somewhere in-between. Dots (a few of which are denoted 270) represent template updates and the horizontal lines (a few of which are denoted 272) represent the template values obtained at the update time. As can be seen, the template value can change significantly throughout the entire range of morphologic variation because each new template is based on the R-wave morphology at the time of the update. This is undesirable.

In contrast, graph 274 provides an abstract representation of variation in R wave morphology (y-axis) over time (x-axis) with template ensemble averaging in accordance with the techniques described above. The dots (a few of which are denoted 276) represent template updates with ensemble averaging, and the horizontal lines (a few of which are denoted 278) represent the template update values. Note the effect of averaging on the template value over time. The template trends toward the center of the range of morphology variation. To allow the template update mechanism to respond to profound changes in morphology, the template update technique includes the aforementioned process/rule (see, steps 212-216 of FIG. 3) that serves to abandon the previous ensemble average (i.e. the active template) in favor of template replacement when the change in morphology is relatively large—as shown in the last (rightmost) template update 280 in graph 274.

Hence, using the template techniques described herein: a) template morphology does not jump to extremes on each update but tends toward a central representation; b) template morphology adapts to short term and long term changes and variability in IEGM morphology; c) template morphology responds appropriately to significant shifts in intrinsic IEGM morphology; and d) at each update the template morphology is protected against adoption of a non-representative template.

Figure 8:
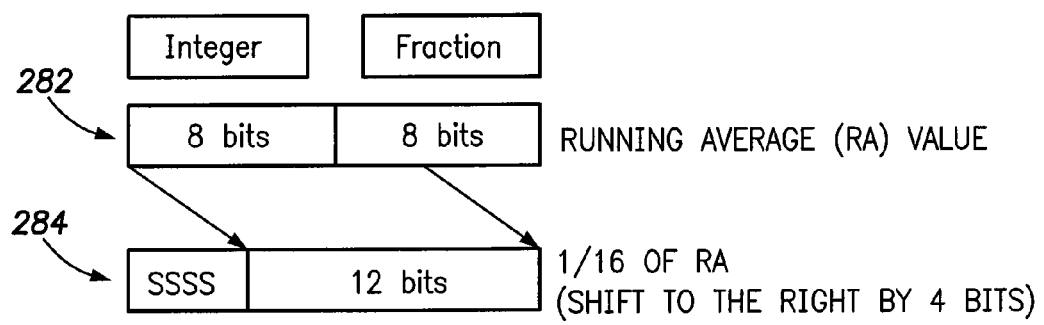
FIG. 8 graphically illustrates an efficient template update procedure that may be exploited by the techniques of FIGS. 3-6.

FIG. 8 graphically illustrates an efficient template update procedure that may be exploited by the techniques of FIGS. 3-5. The recommended method to implement the wave data ensemble average is as a running average 282 for each sample point in the waveform (the ensemble.) When the input waveform data is provided by an eight bit analog-to-digital (A-to-D) converter then each running average is maintained as a sixteen bit value. The upper byte is the integer part and the lower byte is the fractional part, i.e. there is an assumed decimal point between the upper and lower bytes. One sixteenth of a running average value can be formed by shifting the sixteen bit value four bits to the right, with sign bit extension (S), yielding shifted sequence 284. The running average of each sample is then computed as:

$$RA_{new}=RA_{old}-\frac{1}{16}*RA_{old}+\frac{1}{16}Wave_{new}$$

It is important that the fractional part of the ensemble average be maintained from template update to template update, otherwise the $\frac{1}{16}$ Wave$_{new}$ will have an inappropriate (and somewhat unpredictable) effect depending on the absolute value of each wave data point. Note that whenever the non-weighted candidate template is to become the new active template, the device replaces the integer parts of the ensemble running average with the new active template point values and sets the fractional parts to zero.

Hence, using the selective update techniques described above, which are based on weighted ensemble averages, the morphology template is updated so as to average diurnal variation and to track long term changes in IEGM morphology. Other morphology template update procedures typically operate by simply replacing the active template with new data each time the template update process is performed. The improved techniques described herein instead maintain an ensemble running average of the template by computing a running average of each point in the template. To keep the template properly "up to date", the template update operation is preferably attempted several times per day—ideally six to ten times per day. This will keep the template current even if the template update fails periodically. Note that it is expected that the template update operation will fail if conditions are not appropriate for acquiring a new template when the time for an update is reached. Preferably, the device performs various checks (primarily based on rate) to ensure that the patient is not too active during the template update, as activity might introduce noise into the template. If the ventricular rate is high, or there is too much pacing or too many PVC beats, then the template update might initially fail but will be attempted later. It is also expected that as many as half the template updates may not be successful, thus frequent update attempts will help ensure that at least several updates are completed each day.

The overall template update process described herein may be summarized as follows:

A template fiducial point (FP) is established or updated;

Waveform data is collected relative to R detect;

The fiducial point is used to align each waveform data collected;

The template points are extracted around the fiducial point;

When all needed waveforms have been collected an ensemble average (EA) of all waveforms template points is created (i.e. the non-weighted candidate template);

The non-weighted candidate template is combined with the active template as an ensemble running average (i.e. the weighted candidate template);

The two candidate templates (non-weighted and weighted) are validated by comparing them to additional waveform data collected relative to R detect. If the weighted potential template is demonstrated to match the current R-wave morphology then it is set as the new active template. If the weighted potential template does not match but the non-weighted potential template does match then the non-weighted potential template is set as the new active template (indicating that a gross change in R wave morphology has occurred). If neither can be demonstrated to match the current R-wave morphology then the active template is not changed.

The active template therefore is thereby maintained as a substantially correct representation of the morphology of sinus R-waves for this patient.

Although primarily described with respect to examples having an ICD, other implantable medical devices may be equipped to exploit the techniques described herein such as CRT-D devices. Briefly, CRT seeks to normalize asynchronous cardiac electrical activation and resultant asynchronous contractions associated with congestive heart failure (CHF) by delivering synchronized pacing stimulus to both ventricles. The stimulus is synchronized to improve overall cardiac function. This may have the additional beneficial effect of reducing the susceptibility to life-threatening tachyarrhythmias. CRT and related therapies are discussed in, for example, U.S. Pat. No. 6,643,546 to Mathis et al., entitled "Multi-Electrode Apparatus and Method for Treatment of Congestive Heart Failure"; U.S. Pat. No. 6,628,988 to Kramer et al., entitled "Apparatus and Method for Reversal of Myocardial Remodeling with Electrical Stimulation"; and U.S. Pat. No. 6,512,952 to Stahmann et al., entitled "Method and Apparatus for Maintaining Synchronized Pacing". See, also, U.S. Patent Application No. 2008/0306567 of Park et al., entitled "System and Method for Improving CRT Response and Identifying Potential Non-Responders to CRT Therapy" and U.S. Pat. No. 7,653,436 of Schecter, entitled "Global Cardiac Performance."

For the sake of completeness, an exemplary pacer/ICD will now be described, which includes components for performing the functions and steps already described.

Exemplary Pacer/ICD

Figure 9:
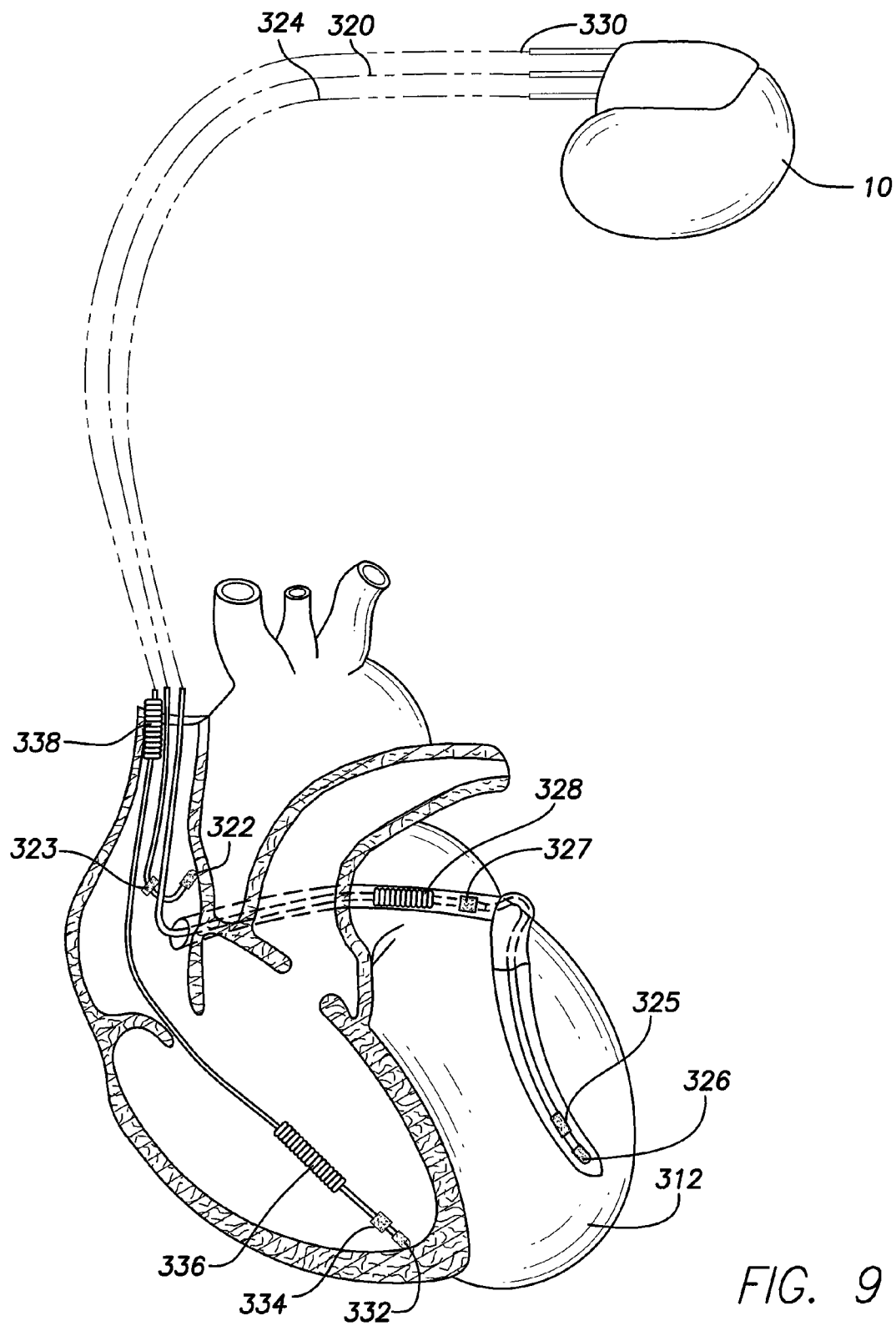
FIG. 9 is a simplified, partly cutaway view, illustrating the device of FIG. 1 along with a set of leads implanted in or on the heart of the patient.

FIG. 9 provides a simplified block diagram of the pacer/ICD, which is a dual-chamber stimulation device capable of treating both fast and slow arrhythmias with stimulation therapy, including cardioversion, defibrillation, and pacing stimulation, as well as capable of performing the template update functions described above. To provide atrial chamber pacing stimulation and sensing, pacer/ICD 10 is shown in electrical communication with a heart 312 by way of a left atrial lead 320 having an atrial tip electrode 322 and an atrial ring electrode 323 implanted in the atrial appendage. Pacer/ICD 10 is also in electrical communication with the heart by way of a right ventricular lead 330 having, in this embodiment, a ventricular tip electrode 332, a right ventricular ring electrode 334, a right ventricular (RV) coil electrode 336, and a superior vena cava (SVC) coil electrode 338. Typically, the right ventricular lead 330 is transvenously inserted into the heart to place the RV coil electrode 336 in the right ventricular apex, and the SVC coil electrode 338 in the superior vena cava. Accordingly, the right ventricular lead is capable of receiving cardiac signals, and delivering stimulation in the form of pacing and shock therapy to the right ventricle.

To sense left atrial and ventricular cardiac signals and to provide left chamber pacing therapy, pacer/ICD 10 is coupled to a "coronary sinus" lead 324 designed for placement in the "coronary sinus region" via the coronary sinus os for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus. Accordingly, an exemplary coronary sinus lead 324 is designed to receive atrial and ventricular cardiac signals and to deliver left ventricular pacing therapy using at least a left ventricular tip electrode 326, left atrial pacing therapy using at least a left atrial ring electrode 327, and shocking therapy using at least a left atrial coil electrode 328. With this configuration, biventricular pacing can be performed. Although only three leads are shown in FIG. 9, it should also be understood that additional stimulation leads (with one or more pacing, sensing and/or shocking electrodes) might be used in order to efficiently and effectively provide pacing stimulation to the left side of the heart or atrial cardioversion and/or defibrillation.

Figure 10:
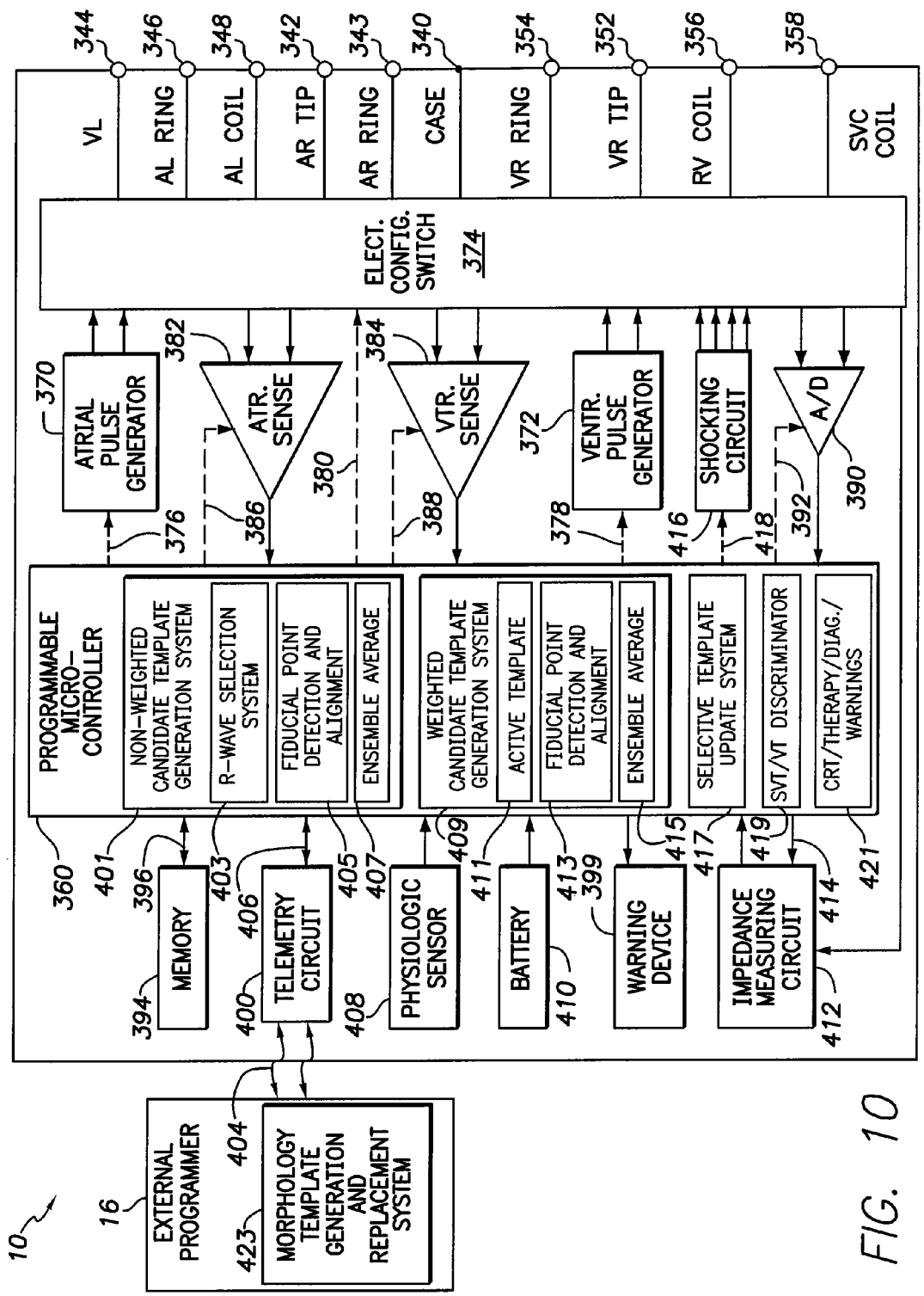
FIG. 10 is a functional block diagram of the device of FIG. 9, illustrating basic circuit elements that provide cardioversion, defibrillation and/or pacing stimulation in the heart and particularly illustrating components for performing the template update techniques of FIGS. 2-8.

A simplified block diagram of internal components of pacer/ICD 10 is shown in FIG. 10. While a particular pacer/ICD is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation as well as providing for the aforementioned impedance-based functions.

The housing 340 for pacer/ICD 10, shown schematically in FIG. 10, is often referred to as the "can", "case" or "case electrode" and may be programmably selected to act as the return electrode for all "unipolar" modes. The housing 340 may further be used as a return electrode alone or in combination with one or more of the coil electrodes, 328, 336 and 338, for shocking purposes. The housing 340 further includes a connector (not shown) having a plurality of terminals, 342, 343, 344, 346, 348, 352, 354, 356 and 358 (shown schematically and, for convenience, the names of the electrodes to which they are connected are shown next to the terminals). As such, to achieve right atrial sensing and pacing, the connector includes at least a right atrial tip terminal ($A_R$ TIP) 342 adapted for connection to the atrial tip electrode 322 and a right atrial ring ($A_R$ RING) electrode 343 adapted for connection to right atrial ring electrode 323. To achieve left chamber sensing, pacing and shocking, the connector includes at least a left ventricular tip terminal ($V_L$ TIP) 344, a left atrial ring terminal ($A_L$ RING) 346, and a left atrial shocking terminal ($A_L$ COIL) 348, which are adapted for connection to the left ventricular ring electrode 326, the left atrial tip electrode 327, and the left atrial coil electrode 328, respectively. To support right chamber sensing, pacing and shocking, the connector further includes a right ventricular tip terminal ($V_R$ TIP) 352, a right ventricular ring terminal ($V_R$ RING) 354, a right ventricular shocking terminal ($R_V$ COIL) 356, and an SVC shocking terminal (SVC COIL) 358, which are adapted for connection to the right ventricular tip electrode 332, right ventricular ring electrode 334, the RV coil electrode 336, and the SVC coil electrode 338, respectively.

At the core of pacer/ICD 10 is a programmable microcontroller 360, which controls the various modes of stimulation therapy. As is well known in the art, the microcontroller 360 (also referred to herein as a control unit) typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 360 includes the ability to process or monitor input signals (data) as controlled by a program code stored in a designated block of memory. The details of the design and operation of the microcontroller 360 are not critical to the invention. Rather, any suitable microcontroller 360 may be used that carries out the functions described herein. The use of microprocessor-based control circuits for performing timing and data analysis functions are well known in the art.

As shown in FIG. 10, an atrial pulse generator 370 and a ventricular/impedance pulse generator 372 generate pacing stimulation pulses for delivery by the right atrial lead 320, the right ventricular lead 330, and/or the coronary sinus lead 324 via an electrode configuration switch 374. It is understood that in order to provide stimulation therapy in each of the four chambers of the heart, the atrial and ventricular pulse generators, 370 and 372, may include dedicated, independent pulse generators, multiplexed pulse generators or shared pulse generators. The pulse generators, 370 and 372, are controlled by the microcontroller 360 via appropriate control signals, 376 and 378, respectively, to trigger or inhibit the stimulation pulses.

The microcontroller 360 further includes timing control circuitry (not separately shown) used to control the timing of such stimulation pulses (e.g., pacing rate, atrio-ventricular (AV) delay, atrial interconduction (A-A) delay, or ventricular interconduction (V-V) delay, etc.) as well as to keep track of the timing of refractory periods, blanking intervals, noise detection windows, evoked response windows, alert intervals, marker channel timing, etc., which is well known in the art. Switch 374 includes a plurality of switches for connecting the desired electrodes to the appropriate I/O circuits, thereby providing complete electrode programmability. Accordingly, the switch 374, in response to a control signal 380 from the microcontroller 360, determines the polarity of the stimulation pulses (e.g., unipolar, bipolar, combipolar, etc.) by selectively closing the appropriate combination of switches (not shown) as is known in the art.

Atrial sensing circuits 382 and ventricular sensing circuits 384 may also be selectively coupled to the right atrial lead 320, coronary sinus lead 324, and the right ventricular lead 330, through the switch 374 for detecting the presence of cardiac activity in each of the four chambers of the heart. Accordingly, the atrial (ATR. SENSE) and ventricular (VTR. SENSE) sensing circuits, 382 and 384, may include dedicated sense amplifiers, multiplexed amplifiers or shared amplifiers. The switch 374 determines the "sensing polarity" of the cardiac signal by selectively closing the appropriate switches, as is also known in the art. In this way, the clinician may program the sensing polarity independent of the stimulation polarity. Each sensing circuit, 382 and 384, preferably employs one or more low power, precision amplifiers with programmable gain and/or automatic gain control, bandpass filtering, and a threshold detection circuit, as known in the art, to selectively sense the cardiac signal of interest. The automatic gain control enables pacer/ICD 10 to deal effectively with the difficult problem of sensing the low amplitude signal characteristics of atrial or ventricular fibrillation. The outputs of the atrial and ventricular sensing circuits, 382 and 384, are connected to the microcontroller 360 which, in turn, are able to trigger or inhibit the atrial and ventricular pulse generators, 370 and 372, respectively, in a demand fashion in response to the absence or presence of cardiac activity in the appropriate chambers of the heart.

For arrhythmia detection, pacer/ICD 10 utilizes the atrial and ventricular sensing circuits, 382 and 384, to sense cardiac signals to determine whether a rhythm is physiologic or pathologic. As used in this section "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the microcontroller 360 by comparing them to a predefined rate zone limit (i.e., bradycardia, normal, atrial tachycardia, atrial fibrillation, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, antitachycardia pacing, cardioversion shocks or defibrillation shocks).

Cardiac signals are also applied to the inputs of an analog-to-digital (A/D) data acquisition system 390. The data acquisition system 390 is configured to acquire intracardiac electrogram signals, convert the raw analog data into a digital signal, and store the digital signals for later processing and/or telemetric transmission to an external device 402. The data acquisition system 390 is coupled to the right atrial lead 320, the coronary sinus lead 324, and the right ventricular lead 330 through the switch 374 to sample cardiac signals across any pair of desired electrodes. The microcontroller 360 is further coupled to a memory 394 by a suitable data/address bus 396, wherein the programmable operating parameters used by the microcontroller 360 are stored and modified, as required, in order to customize the operation of pacer/ICD 10 to suit the needs of a particular patient. Such operating parameters define, for example, pacing pulse amplitude or magnitude, pulse duration, electrode polarity, rate, sensitivity, automatic features, arrhythmia detection criteria, and the amplitude, waveshape and vector of each shocking pulse to be delivered to the patient's heart within each respective tier of therapy. Other pacing parameters include base rate, rest rate and circadian base rate.

Advantageously, the operating parameters of the implantable pacer/ICD 10 may be non-invasively programmed into the memory 394 through a telemetry circuit 400 in telemetric communication with the external device 402, such as a programmer, transtelephonic transceiver or a diagnostic system analyzer. The telemetry circuit 400 is activated by the microcontroller by a control signal 406. The telemetry circuit 400 advantageously allows intracardiac electrograms and status information relating to the operation of pacer/ICD 10 (as contained in the microcontroller 360 or memory 394) to be sent to the external device 402 through an established communication link 404. Pacer/ICD 10 further includes an accelerometer or other physiologic sensor 408, commonly referred to as a "rate-responsive" sensor because it is typically used to adjust pacing stimulation rate according to the exercise state of the patient. However, the physiological sensor 408 may further be used to detect changes in cardiac output, changes in the physiological condition of the heart, or diurnal changes in activity (e.g., detecting sleep and wake states) and to detect arousal from sleep. Accordingly, the microcontroller 360 responds by adjusting the various pacing parameters (such as rate, AV Delay, V-V Delay, etc.) at which the atrial and ventricular pulse generators, 370 and 372, generate stimulation pulses. While shown as being included within pacer/ICD 10, it is to be understood that the physiologic sensor 408 may also be external to pacer/ICD 10, yet still be implanted within or carried by the patient. A common type of rate responsive sensor is an activity sensor incorporating an accelerometer or a piezoelectric crystal, which is mounted within the housing 340 of pacer/ICD 10. Other types of physiologic sensors are also known, for example, sensors that sense the oxygen content of blood, respiration rate and/or minute ventilation, pH of blood, ventricular gradient, pulmonary artery pressure, etc.

The pacer/ICD additionally includes a battery 410, which provides operating power to all of the circuits shown in FIG. 10. The battery 410 may vary depending on the capabilities of pacer/ICD 10. If the system only provides low voltage therapy, a lithium iodine or lithium copper fluoride cell may be utilized. For pacer/ICD 10, which employs shocking therapy, the battery 410 must be capable of operating at low current drains for long periods, and then be capable of providing high-current pulses (for capacitor charging) when the patient requires a shock pulse. The battery 410 must also have a predictable discharge characteristic so that elective replacement time can be detected. Accordingly, pacer/ICD 10 is preferably capable of high voltage therapy and appropriate batteries.

As further shown in FIG. 10, pacer/ICD 10 is shown as having an impedance measuring circuit 412, which is enabled by the microcontroller 360 via a control signal 414. Uses for an impedance measuring circuit include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves, etc. The impedance measuring circuit 412 is advantageously coupled to the switch 374 so that any desired electrode may be used.

In the case where pacer/ICD 10 is intended to operate as an implantable cardioverter/defibrillator device, it detects the occurrence of an arrhythmia, and automatically applies an appropriate electrical shock therapy to the heart aimed at terminating the detected arrhythmia. To this end, the microcontroller 360 further controls a shocking circuit 416 by way of a control signal 418. The shocking circuit 416 generates shocking pulses of low (up to 0.5 joules), moderate (0.5-10 joules) or high energy (11 to 40 joules or more), as controlled by the microcontroller 360. Such shocking pulses are applied to the heart of the patient through at least two shocking electrodes, and as shown in this embodiment, selected from the left atrial coil electrode 328, the RV coil electrode 336, and/or the SVC coil electrode 338. The housing 340 may act as an active electrode in combination with the RV electrode 336, or as part of a split electrical vector using the SVC coil electrode 338 or the left atrial coil electrode 328 (i.e., using the RV electrode as a common electrode). Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 11-40 joules or more), delivered asynchronously (since R-waves may be too disorganized), and pertaining exclusively to the treatment of fibrillation. Accordingly, the microcontroller 360 is capable of controlling the synchronous or asynchronous delivery of the shocking pulses.

Microcontroller 360 also includes various components directed to implementing the aforementioned template update and SVT/VT discrimination techniques. More specifically, a non-weighted candidate morphology template generation system 401 is operative to detect cardiac signals within the patient, assess cardiac rhythm morphology and generate a non-weighted candidate morphology template based on the cardiac rhythm morphology in accordance, for example, with the techniques of FIG. 4. It includes, in this example, an R-wave selection system 403 operative to select R-waves for processing subject the conditions or rules discussed above. A fiducial point detection and alignment system 405 identifies fiducial points within the selected R-waves and aligns the waveforms for ensemble averaging. An ensemble average system 407 ensemble averages the waveforms to create the non-weighted template. The microcontroller also includes a weighted candidate morphology template generation system 409 operative to generate a weighted candidate morphology template based on an ensemble average of the non-weighted candidate morphology template and a previous morphology template in accordance, for example, with the techniques of FIG. 5. It includes, in this example, an active template input system 411 operative to input the active template from memory. A fiducial point detection and alignment system 413 identifies fiducial points within the active template and the non-weighted template generated by system 401. An ensemble average system 415 ensemble averages the active template and the non-weighted template to create the weighted template. A selective template update system 417 is operative to selectively update the active template based on a comparison of additional cardiac rhythm morphology (e.g. newly-detected R-waves) against both the non-weighted and weighted candidate morphology templates in accordance, for example, with the verification techniques of FIG. 3. An SVT/VT discriminator 419 then discriminates SVT from VT based on the currently-active template. A CRT/therapy/diagnostics controller 421 controls the delivery of therapy, including defibrillation shocks and ATP (as well as other forms of therapy that may be appropriate for the patient such as CRT.) Controller 421 also controls the generation of diagnostic data and warning signals in response to detection of any abnormal conditions. Diagnostic data is stored within memory 394. Warning signals may be relayed to the patient via implanted warning device 399 or external device 16.

Depending upon the implementation, the various components of the microcontroller may be implemented as separate software modules or the modules may be combined to permit a single module to perform multiple functions. In addition, although shown as being components of the microcontroller, some or all of these components may be implemented separately from the microcontroller, using application specific integrated circuits (ASICs) or the like.

At least some of the techniques described herein may be performed by, or under the control of, an external device. Accordingly, external device 16 is shown to include morphology template generation and replacement system 413 operative to generate and update morphology templates based on cardiac signals or other parameters sent from the implanted device for subsequent transmission to the implantable device for use therein. In general, any of the components shown within the microcontroller 360 may have corresponding components within the external device. Still further, the external device may include components for setting or adjusting the various programmable thresholds discussed above under clinician supervision.

In general, while the invention has been described with reference to particular embodiments, modifications can be made thereto without departing from the scope of the invention. Note also that the term "including" as used herein is intended to be inclusive, i.e. "including but not limited to."

What is claimed is:

1. A method for use with an implantable medical device for updating a morphology template used to discriminate cardiac rhythms within a patient, the method comprising:
    detecting cardiac signals within the patient, assessing cardiac rhythm morphology and generating a first candidate morphology template based on the cardiac rhythm morphology;
    generating a second candidate morphology template based on an ensemble average of the first candidate morphology template and a previous morphology template;
    selectively updating the previous morphology template based on a comparison of additional cardiac rhythm morphology with both the first and second candidate morphology templates;
    discriminating abnormal cardiac rhythms within the patient using the selectively-updated morphology template; and
    delivering therapy to the patient in response to the detection of an abnormal cardiac rhythm.

2. The method of claim 1 wherein the first candidate morphology template is a non-weighted candidate template.

3. The method of claim 2 wherein detecting cardiac signals, assessing cardiac rhythm morphology and generating the non-weighted candidate template comprises:
    identifying ventricular depolarization waveforms within the cardiac signals for a plurality of ventricular depolarization events;
    identifying fiducial points within the depolarization waveforms;
    aligning the waveforms from the plurality of depolarization events using corresponding fiducial points; and
    ensemble averaging the aligned waveforms to yield the non-weighted candidate waveform.

4. The method of claim 3 wherein identifying depolarization waveforms within the cardiac signals for a plurality of ventricular depolarization events includes rejecting waveforms that are not likely sinus rhythm waveforms.

5. The method of claim 4 wherein rejecting waveforms is performed based on a ventricular rate-based analysis.

6. The method of claim 2 wherein the second candidate morphology template is a weighted candidate template and the previous template is an active template.

7. The method of claim 6 wherein generating the weighted candidate template comprises:
    identifying corresponding fiducial points within the non-weighted candidate template and the active template;
    aligning the non-weighted candidate template with the active template using the corresponding fiducial points; and ensemble averaging the aligned templates to yield the weighted candidate template.

8. The method of claim 6 wherein selectively updating the previous morphology template comprises selectively updating the active template based on a comparison of newly-detected ventricular depolarization events with the non-weighted candidate template and the weighted candidate template.

9. The method of claim 8 wherein selectively updating the active template comprises:
   replacing the active template with the weighted candidate template if the newly-detected ventricular depolarization events substantially match the weighted candidate template;
   replacing the active template with the non-weighted candidate template if the newly-detected ventricular depolarization events substantially match the non-weighted candidate template but not the weighted candidate template; and
   retaining the active template if the newly-detected ventricular depolarization events do not substantially match either the non-weighted candidate template or the weighted candidate template.

10. The method of claim 1 further including recording diagnostic information pertaining to the updating of the morphology template.

11. The method of claim 1 wherein discriminating abnormal cardiac rhythms within the patient includes discriminating ventricular tachycardia (VT) from supraventricular tachycardia (SVT).

12. The method of claim 11 further including controlling therapy in response to a cardiac arrhythmia.

13. The method of claim 1 wherein all of the steps are performed by the implantable medical device.

14. The method of claim 1 wherein at least some of the steps are performed by an external device in communication with the implantable medical device.

15. The method of claim 1 wherein the morphology templates are representative of far-field ventricular depolarization events.

16. A system for use with an implantable medical device for updating a morphology template used to discriminate cardiac rhythms within a patient, the system comprising:
   means for detecting cardiac signals within the patient, assessing cardiac rhythm morphology and generating a first candidate morphology template based on the cardiac rhythm morphology;
   means for generating a second candidate morphology template based on an ensemble average of the first candidate morphology template and a previous morphology template;
   means for selectively updating the previous morphology template based on a comparison of additional cardiac rhythm morphology with both the first and second candidate morphology templates;
   means for discriminating cardiac rhythms within the patient using the selectively-updated morphology template; and
   means for delivering therapy to the patient in response to the detection of an abnormal cardiac rhythm.

* * * * *